(12) United States Patent
Arndt

(10) Patent No.: US 6,835,409 B2
(45) Date of Patent: Dec. 28, 2004

(54) METHOD OF RECORDING FINGERPRINTS ON A RECORDING SURFACE HAVING A THERMOSENSTIVIVE COLOR DEVELOPING LAYER THEREON

(75) Inventor: Douglas C. Arndt, Jacksonville, FL (US)

(73) Assignee: Armor Holdings Forensics, Inc., Jacksonville, FL (US)

( * ) Notice: Subject to any disclaimer, the term of this patent is extended or adjusted under 35 U.S.C. 154(b) by 0 days.

(21) Appl. No.: 10/473,652

(22) PCT Filed: Mar. 5, 2003

(86) PCT No.: PCT/US03/06578
§ 371 (c)(1),
(2), (4) Date: Oct. 2, 2003

(87) PCT Pub. No.: WO03/075759
PCT Pub. Date: Sep. 18, 2003

(65) Prior Publication Data
US 2004/0121065 A1 Jun. 24, 2004

Related U.S. Application Data
(60) Provisional application No. 60/362,759, filed on Mar. 8, 2002.

(51) Int. Cl.[7] .............................................. A61B 5/117
(52) U.S. Cl. ............... 427/1; 427/7; 427/261; 427/288; 427/301; 427/399
(58) Field of Search ................. 427/1, 7, 399, 427/261, 288, 301

(56) References Cited

U.S. PATENT DOCUMENTS

| | | |
|---|---|---|
| 2,235,632 A | 3/1941 | Heinecke |
| 4,029,012 A | 6/1977 | Smith, III et al. |
| 4,182,261 A | 1/1980 | Smith, III et al. |
| 4,262,623 A | 4/1981 | Smith, III et al. |
| 4,983,415 A | 1/1991 | Arndt et al. |
| 5,378,492 A | 1/1995 | Mashiko |
| 5,462,597 A | 10/1995 | Jubran |
| 5,737,071 A | 4/1998 | Arndt |
| 6,027,556 A | 2/2000 | Arndt |
| 6,488,750 B1 | 12/2002 | Arndt |
| 2001/0049340 A1 * | 12/2001 | Tamura et al. ............... 503/204 |

* cited by examiner

Primary Examiner—Kirsten C. Jolley
(74) Attorney, Agent, or Firm—Harold L. Jackson

(57) ABSTRACT

A method of recording fingerprints in which a solution of monohydrogen or dihydrogen ester having an AAV of about 9 or more is applied to a person's fingerprint area with the area then pressed onto a thermosensitive substrate.

9 Claims, 1 Drawing Sheet

METHOD OF RECORDING FINGERPRINTS ON A RECORDING SURFACE HAVING A THERMOSENSTIVIVE COLOR DEVELOPING LAYER THEREON

RELATED APPLICATION

This application is the national stage entry of PCT/US03/06578 filed Mar. 5, 2003 filed 35 USC §371 and claims the benefit of the filing date of provisional application No. 60/362,759, filed Mar. 8, 2002, entitled METHOD OF RECORDING FINGERPRINTS ON A RECORDING SURFACE HAVING A THERMOSENSITIVE COLOR DEVELOPING LAYER THEREON as to all common subject matter.

TECHNICAL FIELD

The present invention relates to a method of recording fingerprints of a person's finger area and more particularly to a method of providing a fingerprint on a recording surface containing a developing substance which reacts with an inkless reagent solution to form a colorant product representative of the ridge pattern of a person's fingerprint area. It is to be noted that, as used herein, the term "fingerprint" encompasses prints of an individual's hands or fingers or feet, such as those taken from newly born infants.

DESCRIPTION OF THE PRIOR ART

Fingerprints have become a universal method of identifying individuals. Fingerprint identification is an exacting science since two impressions of even the same fingerprint can appear different due to variations in the amount of chemical, such as ink deposited onto the recording surface, chemical migration and changes in the finger itself. To determine an exact correspondence a trained fingerprint technician or an automated machine reader compares the pattern of ridge endings and ridge bifurcations (minutiae) which are invariant with time on each person's fingerprint.

The prior art has recognized that any viable fingerprint identification system requires a clear distinct print pattern with a minimum of chemical migration between adjacent ridges. An additional requirement for any voluntary print identification system, such as to be utilized commercially with checks, credit verification, verification of the recipient of a package or document, and the like, is that it be inoffensive to the person whose fingerprint is being obtained. Carbon based ink fingerprinting systems are particularly offensive because the ink stains the finger and must be removed. Furthermore, such systems tend to result in a smudging of the prints when the fingerprint documents, such as checks, etc, are handled. Inkless fingerprinting systems have been developed to overcome the above disadvantages of carbon based ink systems.

See, for example, U.S. Pat. Nos. 4,182,261 and 4,262,623 assigned to the assignee of this application and the references cited therein. Inkless systems generally rely on a chemical reaction between an invisible reagent deposited onto a porous recording surface such as paper or a card in the form of a latent fingerprint image and a developer which is applied to the surface before or after the application of the reagent. The reagent and developer react chemically to form a colored pattern, on the recording surface, representative of the ridge pattern of a person's fingerprint. A large number of suitable reagent developer pairs for this type of application are disclosed in U.S. Pat. Nos. 4,029,012 and 4,182,261. It has also been suggested in U.S. Pat. No. 2,235,632 that the latent invisible fingerprint deposited from the person's finger on the recording surface may be developed by a colorless powder, or volatile vapors comprising the developer or by the application of heat or intense light.

The application of a developer to the fingerprint paper or card just before or after the finger has deposited the reagent to provide the chemical reaction necessary to transform the invisible latent image into a visible one is time consuming and requires that an additional chemical be applied to the recording surface as compared with carbonized ink systems. The application of heat or intense light suffers from the obvious disadvantage that additional appendages to the fingerprinting apparatus, such as a heat or light source, may be required. Also, the operator of the fingerprinting apparatus cannot immediately judge whether or not the fingerprint taken is acceptable, since he or she has to wait until the print is developed by the application of heat or light.

U.S. Pat. No. 4,983,415 incorporated herein by reference, discloses an inkless system in which an acidic metal, e.g., a ferric salt solution, is used to develop the color former inherent in ordinary thermal paper. While the '415 system provides an excellent permanent print, the ferric chloride solution is very acidic and therefor corrosive to metals. The system, depending upon the metallic salt used, may also react slowly with common thermal papers and provide an off black image, e.g., greenish-gray. Such metallic salt solutions are also fairly expensive.

There is a need for an inkless fingerprint method which relies on thermosensitive paper to develop the image and utilizes relatively inexpensive reagents to react with the paper.

SUMMARY OF THE INVENTION

In accordance with the present method a thermosensitive recording surface is provided which contains a thermosensitive color developing layer, the layer comprising chromogenic dyes, an organic acid developer reactive with the dye to develop a color and thermosensitive barrier for separating the acid from the dye. A solution of a monohydrogen or dihydrogen ester having an AAV value of about 9 or more is applied to the fingerprint area of the person to be printed and the fingerprint area is then pressed onto the recording surface whereby the solution reacts with the dye to provide a colorant product representative of the pattern of ridges and ridge endings of the fingerprint area.

BRIEF DESCRIPTION OF THE PREFERRED EMBODIMENT

Figure 1:
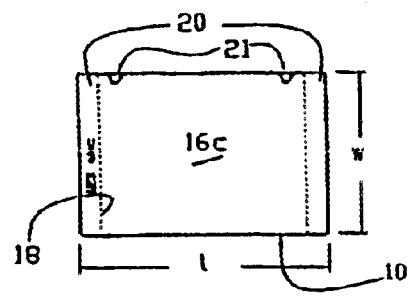
FIG. 1 is a top plan view of a self-contained fingerprint ink applicator and recording surface for use with the present invention.

The following description is provided to enable any person skilled in the art to make and use the invention and set forth the best mode contemplated by me of carrying out the invention.

In carrying out the invention a solution of an ester of the monohydrogen or dihydrogen type such as a mono or dialkyl phosphate ester, is provided and stored in a suitable dispensing pad which is non-reactive with the solution. The pad should provide sufficient solution to wet the ridge pattern of a person's finger (foot or palm) without causing deleterious solution migration between the ridges. Suitable materials for the pad include gauze, felt, porous plastics, porous ceramics, etc. The reservoir need not be in the form of a pad but may be in the form of a sheet or other suitable form.

An ester suitable for use with the present method comprises a reaction of a mineral or organic acid with alcohol to form a monohydrogen or dihydrogen ester which is liquid at ambient temperature and has an acid activity value ("AAV") of at least about 9. An acid activity value of 9 means that one gram of the ester will neutralize 9 milligrams of potassium hydroxide (KOH) sufficient to provide a reasonably rapid and dark imaging of a fingerprint on a thermosensitive recording surface as will be described in more detail.

I have found that mono and dialkyl phosphates esters, such as phenyl acid phosphate, butyl acid phosphate and 2-ethyl-hexyl acid phosphate are satisfactory as the mineral acid component of the esters. Butyl acid phosphate is substantially nonhazardous and therefor may be preferred.

These short-chain, linear and branched phosphate esters are acidic and offer surfactant, lubricant and corrosion resistant properties. Lamchem BAP® (a mixture of butyl dihydrogen phosphate and butyl monohydrogen phosphate) manufactured by Lambent Technologies, a Petroferm Company, is the chemical of choice. It has an average acid activity number of approximately 480 KOH/g, i.e., running between about 450 to 510 AAV.

It should be noted that, while phosphoric acid will develop the leuco and furan dyes precursors used in making conventional thermosensitive paper, such acids, if not sufficiently diluted, may cause the color former in the paper to revert to a colorless state, i.e., the image disappears after the chromogenic reaction reaches completion because of excess available protons.

Other acids that can be substituted for the phosphoric acids include: tert-butylphosphonic acid, the alkyl monoesters (ethyl, methyl, propyl, butyl, pentyl, hexyl, octyl, etc) of valeric acid, caprylic acid, and capric acid; 2-aminoethyldihydrogen phosphate, and the monobasic and dibasic aliphatic esters (oleyl, myristyl, dodecyl, palmityl, and stearyl, etc) of phosphoric acid.

It is to be noted that the monoester or diester must be a stable liquid at ambient conditions and must have sufficient acid activity, i.e., about 9.0 AAV, and preferably more. It is to be noted that higher acid activity values produce correspondingly faster and darker prints up to the point where over acidification occurs, i.e., the image disappears. An AAV of 100–150 give high contrast and an AAV of 330–510 gives a very good contrast and a substantially true black color.

By necessity at least one hydrogen atom having acid functionality must be present on the molecule to serve as an electron receptor. For example, the binary acid (2H+) can only be esterified as monobasic to leave one available hydrogen ion (i.e., proton), but a tertiary acid (3H+) can be esterified as either monobasic (dihydrogen) or dibasic (monohydrogen). Other practical considerations such as cost, availability, material incompatibilities, and possible health and environmental hazards limit the range of reagents that must be used. I have found that an ester for use in my invention may be comprised of the monoalkyl and dialkyl phosphates of ethanol, methanol, and n-butanol.

See U.S. Pat. No. 4,983,415 for an example of thermosensitive paper useful for the present invention.

The recording surface may comprise a conventional thermosensitive recording paper as used in facsimile apparatus. Such paper, as discussed previously, includes a thermosensitive color-developing layer which comprises a chromogenic dye and an organic acid developer reactive with the dye to develop a color. A thermosensitive barrier for separating the acid from the dye may also be included.

To record a fingerprint in accordance with my invention, a person's finger, palm or foot is coated with the solution of the chosen chemical ester by pressing it against the ester-containing pad. The fingerprint is then pressed or rolled onto the recording area surface. The ester reacts with the chromogenic dye to form a substantially permanent perceivable colorant (generally black) precipitate within the thermosensitive layer representative of the ridge pattern of the person's fingerprint area.

Figure 2:
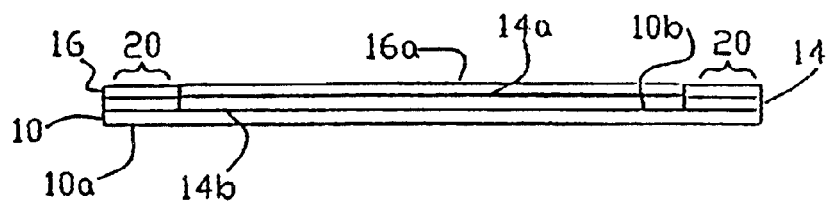
FIG. 2 is a side elevational view of the applicator of FIG. 1.
Figure 2A:
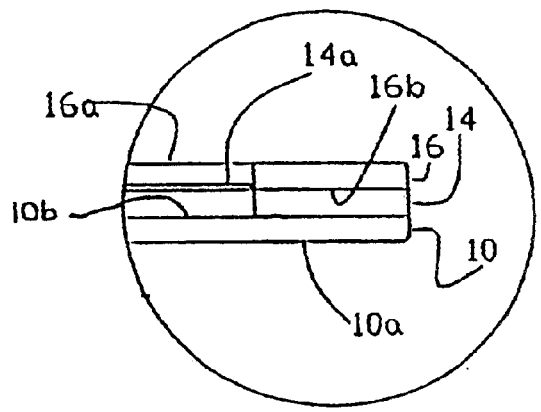
FIG. 2a is a blow up view of the right corner of the applicator of FIG. 1.
Figure 3:
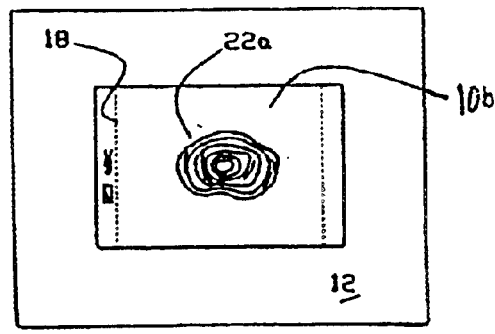
FIG. 3 is a top plan view of the applicator of FIG. 1 with the central portion of the two top sheets removed exposing the upper (recording) surface of the bottom sheet (affixed to a document) with a facsimile of a fingerprint thereon.

I have found the present method of recording fingerprints to be particularly useful in a self-contained ester applicator/recording surface as illustrated in FIGS. 1–3.

The self-contained applicator comprises three thin sheets of a suitable material in which the bottom or base sheet 10 has an adhesive on the lower surface 10a thereof for affixing the applicator to a document 12, etc. and a thermosensitive top layer 10b. An intermediate sheet 14, having a pad such as a gauze layer 14a on the central portion of the upper surface for receiving the ester, is sandwiched between the base sheet 10 and a top sheet 16. The top sheet has an upper surface for accommodating a printed message or the like. The sheets are bonded together along peripheral margins 20. Perforations 18, extending through the top and intermediate sheets, allow the central portion of the top sheet to be removed exposing the pad 14a containing the liquid ester for application to a person's fingertip. The central portion of the intermediate sheet can then be removed exposing the central portion of the base sheet so that the liquid ester on the ridges of the fingertip can be transferred to the recording surface 10b as is illustrated in FIG. 3. See 22a of FIG. 3. Notches 21 in the top and intermediate sheets facilitate the removal of the central portions of these sheets. A more detailed discussion of a general purpose ink applicator/recording surface is contained in my co-pending PCT application entitled "Self Contained Fingerprint Ink Applicator and Recording Substrate" filed on even date herewith and the contents of such application are incorporated herewith by reference.

It is to be noted that the monohydrogen and dihydrogen esters referred to above are substantially noncorrosive and can readily be used with equipment having metal components, rendering it more useful for producing inexpensive, off-the-shelf disposable ink pads, such as pad 14a. In addition, esters are readily available as off-the-shelf chemicals thereby eliminating the labor costs for mixing reagents.

What is claimed is:

1. A method of recording prints of a person's fingertip, palm or foot comprising:

a) providing a thermosensitive recording surface containing a thermosensitive color developing layer, the layer comprising a chromogenic dye, an organic acid developer reactive with the dye to develop a color and a thermosensitive barrier for separating the acid from the dye;

b) applying a solution of a chemical compound containing monohydrogen and/or dihydrogen esters in a liquid state, the compound having an AAV value of about 9 or more, to the fingerprint, palm print or foot to be printed; and c) depositing the solution from the ridges of the fingerprint, palm print or footprint pattern area to the recording surface whereby the chemical compound reacts with the dye to provide a colorant product representative of the ridge pattern of the finger, palm or foot of said person.

2. The method of claim 1 wherein the monohydrogen and/or dihydrogen esters comprise one or more compounds selected from the group consisting of phenyl acid phosphate, butyl acid phosphate and 2-ethyl-hexyl acid phosphate, tert-butylphosphonic acid, the alkyl monoesters of valeric acid, caprylic acid, and capric acid, 2-aminoethyldihydrogen phosphate, and the monobasic and dibasic aliphatic esters of phosphoric acid, monoalkyl and dialkyl phosphates of ethanol, methanol, and n-butanol.

3. The method of claim 2 wherein the ester comprises a mixture of butyl dihydrogen phosphate and butyl monohydrogen phosphate having an AAV within the range of about dihydrogen phosphate and butyl monohydrogen phosphate having an AAV within the range of about 330 to 510.

4. The method of claim 3 wherein the ester(s) has an AAV within the range of about 450 to 510.

5. The method of claim 2 wherein the alkyl monoesters are selected from the group consisting of ethyl, methyl, propyl, butyl, pentyl, hexyl and octyl and the aliphatic esters are selected from oleyl, myristyl, dodecyl, palmityl, and stearyl.

6. The method of claim 1 wherein the ester(s) has an AAV within the range of about 100 to 150.

7. The method of claim 1 wherein the ester(s) has an AAV within the range of about 330 to 510.

8. The method of claim 1 wherein the ester comprises monoalkyl and dialkyl phosphates of ethanol, methanol and/or n-butanol.

9. The method of claim 1 wherein the ester(s) has an AAV within the range of about 150 to 330.

* * * * *

UNITED STATES PATENT AND TRADEMARK OFFICE
CERTIFICATE OF CORRECTION

PATENT NO. : 6,835,409 B2
DATED : December 28, 2004
INVENTOR(S) : Douglas C. Arndt It is certified that error appears in the above-identified patent and that said Letters Patent is hereby corrected as shown below:

Title page,
Item [54], Title, "THERMOSENTIVIVE" should read -- THERMOSENSITIVE --.

Column 1,
Line 8, after "2003 filed" insert -- under --.

Column 3,
Line 9, "pad)" should read -- pad, --.

Column 5,
Line 12, after "of" insert -- : -- and after "phosphate" delete "," and insert -- ; --.
Line 13, after "butyl acid phosphate" insert -- ; -- and delete "and".
Line 13, after "2-ethyl-hexyl acid phosphate" delete "," and insert -- ; --.
Line 14, after "acid" insert -- ; --.
Line 15, after "acid" (third occurrence) delete "," and insert -- ; --.
Line 16, after "phosphate" delete "," and insert -- ; --.
Line 17, after "acid" delete "," and insert -- ; and --.

Column 6,
Lines 1 and 2, delete "dihydrogen phosphate and butyl monohydrogen phosphate having an AAV withn the range of about".

Signed and Sealed this

Twenty-fourth Day of May, 2005

JON W. DUDAS
*Director of the United States Patent and Trademark Office*